(12) United States Patent
Cao et al.

(10) Patent No.: US 8,545,859 B2
(45) Date of Patent: Oct. 1, 2013

(54) USE OF ACRYLATES COPOLYMER AS WATERPROOFING AGENT IN PERSONAL CARE APPLICATIONS

(75) Inventors: Hongjie Cao, Somerville, NJ (US); Gary T. Martino, Monmouth Junction, NJ (US); Samuel A. Vona, Jr., Bound Brook, NJ (US)

(73) Assignee: Akzo Nobel N.V., Arnhem (NL)

( * ) Notice: Subject to any disclaimer, the term of this patent is extended or adjusted under 35 U.S.C. 154(b) by 1497 days.

(21) Appl. No.: 10/723,341

(22) Filed: Nov. 26, 2003

(65) Prior Publication Data

US 2005/0112080 A1   May 26, 2005

(51) Int. Cl.
*A61K 8/02* (2006.01)
*A61K 8/72* (2006.01)
*A61K 8/81* (2006.01)
*C08F 20/10* (2006.01)

(52) U.S. Cl.
USPC ............... 424/401; 424/70.11; 424/70.16; 526/323.2

(58) Field of Classification Search
None
See application file for complete search history.

(56) References Cited

U.S. PATENT DOCUMENTS

| | | | | |
|---|---|---|---|---|
| 4,085,264 A | * | 4/1978 | Seib et al. | 525/360 |
| 4,172,122 A | * | 10/1979 | Kubik et al. | 424/59 |
| 5,139,877 A | * | 8/1992 | Self et al. | 428/421 |
| 5,204,090 A | | 4/1993 | Han | |
| 5,288,493 A | | 2/1994 | Martino et al. | |
| 5,853,700 A | * | 12/1998 | Gormley et al. | 424/47 |
| 5,972,354 A | | 10/1999 | de la Poterie et al. | |
| 6,010,686 A | | 1/2000 | de la Poterie et al. | |
| 6,106,577 A | | 8/2000 | Audousset et al. | |
| 6,221,389 B1 | * | 4/2001 | Cannell et al. | 424/450 |
| 6,322,776 B1 | | 11/2001 | Ortega, II et al. | |
| 6,503,495 B1 | | 1/2003 | Alwattari et al. | |
| 6,524,565 B1 | | 2/2003 | Loginova et al. | |
| 2002/0035046 A1 | | 3/2002 | Lukenbach et al. | |
| 2002/0076390 A1 | | 6/2002 | Kantner et al. | |
| 2002/0142014 A1 | | 10/2002 | Afriat et al. | |
| 2003/0031637 A1 | | 2/2003 | Loginova et al. | |

FOREIGN PATENT DOCUMENTS

| | | |
|---|---|---|
| EP | 1 486 514 A1 | 12/2004 |
| JP | 5-17320 | 1/1993 |
| JP | 2001-10942 | 1/2001 |
| JP | 2001-503063 | 3/2001 |
| JP | 2003-166829 | 6/2003 |
| JP | 2005-2207 | 1/2005 |

OTHER PUBLICATIONS

Principles of polymerization. George Odian. $3^{rd}$ Edition, p. 335, 1999 (3 pages).*
"Acrylates/C12-22 Alkylmethacrylate Copolymer (Allianz™ OPT): A New Polymer for Sunscreen Water Resistance Through Oil Phase Thickening", *Cosmetics and Toiletries Manufacture Worldwide*, Aston Publishing Group, pp. 185-190 (2002).
"Sunscreen Drug Products for Over-The-Counter Human use," 21 CFR Part 352, Subpart D (Fed. Reg./ vol. 64, No. 98 (May 21, 1999).
Taiwan Search Report dated Aug. 3, 2011 for Application No. 03136392, English Translation.
English Translation of Japanese Office Action mailed Jul. 13, 2010.
English Translation of Japanese Publication No. 5-17320, Jan. 1993.
English Translation of Japanese Publication No. 2003-166829, Jun. 2003.

* cited by examiner

*Primary Examiner* — Lakshmi Channavajjala
(74) *Attorney, Agent, or Firm* — Norris McLaughlin & Marcus, P.A.

(57) ABSTRACT

The present invention relates to the use of acrylate copolymers, which provide excellent water resistance to personal care products without the undesirable waxy, greasy or heavy feel. Further, these acrylate copolymers are easy for manufacturers to use as they can be easily incorporated into the water phase without special processing.

8 Claims, No Drawings

USE OF ACRYLATES COPOLYMER AS WATERPROOFING AGENT IN PERSONAL CARE APPLICATIONS

BACKGROUND OF THE INVENTION

The present invention relates to the use of acrylate copolymers as water proofing agents in personal care products.

Many personal care products rely on water proofing agents for their overall functionality. For example, there is a consumer need for mascaras, which will not come off upon crying, and sunscreen lotions which will not come off during swimming. Although there exist many personal care products which claim water resistance or water proofing, there is a need for longer lasting water resistance with improved aesthetics. Many existing products that claim water resistance are waxy, greasy or heavy in feel, making them undesirable to consumers. Further, many of the agents currently used in personal care products to impart water resistance are difficult to handle or incorporate into the formulations.

A poly(vinylpyrrolidone/eicosene)copolymer currently used in many personal care formulations to impart water proofing, is oil soluble, and results in a formulation with an unpleasant greasy, waxy or heavy afterfeel. Further, it is difficult to incorporate into products in that it cannot just be mixed in at any point during processing. This poly(vinylpyrrolidone/eicosene) copolymer may also increase the formulation viscosity dramatically, resulting in difficulties in formulating products with desired properties.

Consumers are demanding not only improved water resistance of their personal care products, but also smooth, creamy formulations, which are neither waxy nor heavy and greasy in feel. Manufacturers are demanding that such water proofing agents be easy to incorporate into products, particularly in the aqueous phase, without the need for heat, neutralization, or other special processing, thus allowing greater formulation versatility.

Surprisingly, it has now been found that the use of acrylate copolymers provide excellent water resistance to personal care products without the undesirable waxy, greasy or heavy feel. Further, these acrylate copolymers are easy for manufacturers to use as they can be easily incorporated into the water phase without special processing.

SUMMARY OF THE INVENTION

The present invention relates to the use of acrylate copolymers, which provide excellent water resistance to personal care products without the undesirable waxy, greasy or heavy feel. Further, these acrylate copolymers are easy for manufacturers to use as they can be easily incorporated into the water phase without special processing.

Acrylate copolymers, as used herein, is intended to mean polymers consisting of at least two acrylate monomers, which will result in a copolymer that is water dispersible.

DETAILED DESCRIPTION OF THE INVENTION

The present invention relates to the use of acrylate copolymers, which provide excellent water resistance to personal care products and are easy for manufacturers to use as they can be easily incorporated into the water phase without special processing. Further, these acrylates copolymers do not give undesirable greasy, waxy or heavy skin feel.

The acrylate copolymer is a polymer formed from at least two monomers selected from acrylic and methacrylic acids, and esters and/or amides of acrylic acid or methacrylic acid and is intended to include in particular methyl(meth)acrylate, ethyl(meth)acrylate, propyl(meth)acrylate, butyl(meth)acrylate, isobutyl(meth)acrylate, hydroxypropyl methacrylate, and hydroxyethyl methacrylate. Particularly suitable monomers are butyl acrylate, methylmethacrylate, and methacrylic acid. Such acrylate polymers are water dispersible and exclude those having more than trace amounts of hydrophobic monomers which contain an alkyl group of greater than or equal to C6, more particularly C8. Most particularly suitable acrylate polymers are those with a net anionic charge at a pH of above about 4, though one skilled in the art would understand that this net anionic charge would increase as the pH increases.

In a particularly suitable embodiment, the acrylate copolymer contains about 1 to 85% butyl acrylate, about 1 to 87% methylmethacrylate, and about 1 to 25% methacrylic acid, by weight. In a more particularly suitable embodiment, the acrylate copolymer contains about 38 to 48% butyl acrylate, about 39 to 49% methylmethacrylate, and about 8 to 18% methacrylic acid, by weight.

The acrylate copolymer is typically provided in the form of an emulsion which is a thin, non-viscous liquid as a 45% polymer-in-water emulsion. The acrylate copolymer may also be provided in a dry form.

The acrylate copolymer may be used in any amount necessary to achieve the desired functionality and properties of the personal care products. Typically, it will present in an amount of from about 0.2 to 10%, particularly in an amount of about 0.5 to 4%, more particularly about 1 to 2%, by weight of the personal care composition.

The acrylate copolymer may be added to the personal care composition at any feasible point in the process. In an emulsion formula, the acrylates copolymer can be added to the aqueous phase prior to emulsification, during the emulsification or heating stage, during the cool down stage, or after cool down. The acrylate copolymer is dispersible in cold (room temperature) water without the need for added heat. Further, there is no need to neutralize the polymer or apply any other special processing to achieve sufficient dispersion in water or other aqueous media.

Neutralization is not only unnecessary, but no substantial neutralization is particularly suitable for the acrylate copolymers of this invention. When neutralization is carried out, it is done using bases and methods known in the art, and is preferably not to the point of complete polymer neutralization resulting in polymer solubilization. However, it is understood that this invention includes those embodiments in which the acrylate copolymers are neutralized, even 100% neutralized.

The personal care composition or product can be any desired by the consumer for use on the skin, eyelashes or eyebrows, including without limitation, cosmetic compositions such as mascara, facial foundations, eyeliners, lipsticks, and color products; skin care compositions such as moisturizing lotions and creams, skin treatment products, skin protection products in the form of an emulsion, liquid, stick, or a gel; sun care compositions such as sunscreens, sunscreen emulsions, lotions, creams, sunscreen emulsion sprays, liquid/alcohol sunscreen sprays, sunscreen aqueous gels, broad spectrum sunscreens with UVA and UVB actives, sunscreens with organic and inorganic actives, sunscreens with combinations of organic and inorganic actives, suntan products, self-tanning products, and after sun products etc. Particularly suitable compositions are personal care emulsions, more particularly suitable are sun care compositions such as sunscreen emulsions and sunscreen emulsion sprays. The personal care composition may be in any form, including without limitation in sprays, emulsions, lotions, gels, liquids, sticks, waxes, pastes, powders, and creams.

The personal care composition will contain other components commonly used in the industry, and these will vary greatly depending upon the type of composition and the functionality and properties desired. Without limitation, these components include thickeners, suspending agents, emulsifiers, UV filters, sunscreen actives, humectants, moisturizers, emollients, oils, waxes, solvents, chelating agents, vitamins, antioxidants, botanical extracts, silicones, neutralizing agents, preservatives, fragrances, dyes, pigments, conditioners, polymers, antiperspirant active ingredients, anti-acne agents, anti-dandruff actives, surfactants, exfoliants, film formers, propellants, tanning accelerator, hair fixatives and colors. The acrylate copolymers of the present invention are compatible with most other components used in conventional personal care compositions. For example, sunscreen compositions may contain at least one component selected from the group comprising organic UV filters, inorganic UV actives, UVA and/or UVB sunscreen actives, octinoxate, octisalate, oxybenzone, homosalate, octocrylene, avobenzene, titanium dioxide, starch, conditioning agents, emulsifiers, rheology modifiers and thickeners, neutralizers, emollients, solvents, film formers, moisturizers, antioxidants, vitamins, chelating agents, preservatives, fragrances, and zinc oxide. Skin care and cosmetic compositions may contain at least one component selected from the group consisting of vitamins, anti-aging agents, moisturizers, emollients, emulsifiers, surfactants, preservatives, pigments, dyes, colors and insect repellents.

The resultant personal care compositions are water resistant. Using the test described in the example section below, the acrylate copolymers of this invention are water resistant for at least 40 minutes, more particularly at least 60 minutes, most particularly at least 80 minutes. The SPF retention provided by the polymer in a sunscreen is more than 60%, preferably more than 80%, and more preferably more than 90% after 80 minutes immersion in water. Sunscreens with the polymer have shown higher SPF value comparing with the same sunscreen base without polymer, particularly after immersion in water.

The resultant personal care compositions have excellent feel on the skin, exhibiting no noticeable waxiness, greasiness or heavy feeling. Further, the compositions have excellent rub-off resistance, film forming properties, and moisturizing effects.

EXAMPLES

The following examples are presented to further illustrate and explain the present invention and should not be taken as limiting in any regard. All percents used are on a weight basis.

The following ingredient is used in the examples:

Dermacryl® AQF polymer, Acrylates Copolymer, 45% active polymer-in-water emulsion (commercially available from National Starch and Chemical Company, Bridgewater, N.J., USA)

Example 1

Water Resistant Sunscreen Cream

| | | % W/W | |
|---|---|---|---|
| Ingredient | INCI Designation | Blank | Formula 1 |
| Phase A | | | |
| D.I. water | Water | 48.90 | 44.50 |
| Pricerine 9088 | Glycerine 99.5% | 5.00 | 5.00 |
| Carbopol 940(2%) | Carbomer | 10.00 | 10.00 |
| Pemulen TR-2 | Acrylates/C10-30 Alkyl Acrylate Cross Polymer | 0.20 | 0.20 |
| Phenonip | Phenoxyethanol and Methyl Paraben and Butyl Paraben and Ethyl Paraben and Propyl Paraben | 1.00 | 1.00 |
| TEA 99% | Triethanolamine | 0.40 | 0.40 |
| Dermacryl AQF (45% active) polymer | Acrylates Copolymer | 0.00 | 4.40 |
| Phase B | | | |
| Neo Heliopan AV | Ethylhexyl Methoxycinnamate | 7.50 | 7.50 |
| Neo Heliopan BB | Benzophenone-3 | 6.00 | 6.00 |
| Neo-Heliopan OS | Ethylhexyl Salicylate | 4.00 | 4.00 |
| Uvinul M-539T | Octocrylene | 9.00 | 9.00 |
| Protachem GMS-450 | Glyceryl Stearate | 2.50 | 2.50 |
| Pristerine 4911 | Stearic Acid | 2.50 | 2.50 |
| Prisorine 3515 | Isostearyl Alcohol | 1.00 | 1.00 |
| Amphisol | DEA-Cetyl Phosphate | 2.00 | 2.00 |
| Total | | 100.00 | 100.00 |
| Viscosity* (cps) | | 76,000 | 84,000 |

*Viscosity was measured using Brookfield DV-I, spindle #6 at 10 rpm, 23° C.

Mixing procedure: Water and glycerine were combined at room temperature with propeller mixing, Carbopol 940 and Pemulen TR-2 were dispersed in the water/glycerin mixture and mixed until smooth. The rest of the phase A ingredients were then added in order while stirring. Phase A and B were heated separately to 70-75° C. with propeller mixing. When both phase A and phase B reached temperature, B was added to A with vigorous mixing. The temperature was kept at 75° C. for an additional 15 minutes, then the heat was dispersed and cooling was started with moderate mixing until ambient temperature was reached.

Example 2

Water Resistant Sunscreen Spray Lotion

| Ingredient | INCI name | % w/w Formula 2 |
|---|---|---|
| Phase A | | |
| Neo Heliopan OS | Ethylhexyl Salicylate | 5.00 |
| Escalol 567 | Benzophenone-3 | 3.00 |
| Homosalate | Homosalate | 7.00 |
| Neo Heliopan AV | Ethylhexyl Methoxycinnamate | 7.50 |
| Finsolv TN | C12-15 Alkyl Benzoate | 5.00 |
| Stearyl Alcohol | Stearyl Alcohol | 1.50 |
| Phase B | | |
| D.I. Water | Water | 62.00 |
| Versene NA | Disodium EDTA | 0.10 |
| Arlatone V-100 | Steareth-100 (and) Steareth-2 (and) Glyceryl Stearate Citrate (and) Sucrose (and) Mannan (and) Xanthan Gum | 1.50 |
| Pricerine 9088 | Glycerine 99.5% | 2.00 |
| Dermacryl AQF (45% active) polymer | Acrylates Copolymer | 4.40 |
| Phase C | | |
| Phenonip | Phenoxyethanol (and) Methylparaben (and) Butylparaben (and) Ethylparaben (and) Propylparaben | 1.00 |

Mixing Procedure: Arlatone V-100 was dispersed in cold water until homogeneous. The remaining ingredients of the phase B were mixed in and heated to 75-80° C. Phase A was mixed in and heated to 75-80° C. Phase A was slowly added to phase B while stirring with high speed and then stirred for 10 minutes. The mixture was homogenized for 2 minutes. And Part C was added and mixed until uniform.

Example 3

Water Resistant Sunscreen Emulsion Spray

| Ingredient | % w/w | | | |
|---|---|---|---|---|
| | Formula 3 | Formula 4 | Formula 5 | Formula 6 |
| Phase A | | | | |
| D.I. Water | 74.11 | 78.51 | 74.26 | 76.51 |
| Disodium EDTA | 0.04 | 0.04 | 0.04 | 0.04 |
| Pemulen TR-1 | 0.20 | 0.20 | 0.20 | 0.20 |
| Glycerin 99.5% | 3.00 | 3.00 | 3.00 | 3.00 |
| Phenonip | 1.00 | 1.00 | 1.00 | 1.00 |
| Dermacryl AQF (45% active) polymer | 4.40 | 0.00 | 0.00 | 0.00 |
| Phase B | | | | |
| Ethylhexyl Methoxycinnamate | 7.50 | 7.50 | 7.50 | 7.50 |
| Ethylhexyl Salicylate | 5.00 | 5.00 | 5.00 | 5.00 |
| Benzophenone-3 | 4.00 | 4.00 | 4.00 | 4.00 |
| Cetearyl Alcohol | 0.30 | 0.30 | 0.30 | 0.30 |
| Sorbitan Oleate | 0.45 | 0.45 | 0.45 | 0.45 |
| PVP/Eicosene Copolymer | 0.00 | 0.00 | 0.00 | 2.00 |
| Phase C | | | | |
| Acrylates/C12-22 Alkylmethacrylate Copolymer | 0.00 | 0.00 | 4.25 | 0.00 |
| Phase D | | | | |
| Triethanolamine | q.s. to pH 6.5 | q.s. to pH 6.5 | q.s. to pH 6.5 | q.s. to pH 6.5 |
| Total | 100.00 | 100.00 | 100.00 | 100.00 |

Mixing procedure: Phase A and B were combined separately and heated to 75° C. with mixing. Phase B was added to A with vigorous mixing and mixed at 75° C. for 15 minutes. Cooling was then started and continued until the temperature dropped below 40° C. Phase C was added (for Formula 5 only) and mixed thoroughly. Phase D was added to adjust pH at the end.

| Viscosity (Brookfield DV-I, spindle #6@10 rpm, measured at 23° C.): | |
|---|---|
| Formula 3 (Dermacryl AQF polymer): | 4200 cps |
| Formula 4 (Blank): | 5800 cps |
| Formula 5 (Acrylates/C12-22 Alkylmethacrylate Copolymer): | 9100 cps |
| Formula 6 (PVP/Eicosene Copolymer): | 12100 cps |

The resultant sunscreen spray emulsion has no significant viscosity increase by addition of Dermacryl AQF polymer, and the formula has excellent spray patterns. The formula with Dermacryl AQF polymer was similar in viscosity to the base with no polymer and less viscous than a similar formula with Acrylates/C12-22 Alkylmethacrylate Copolymer or PVP/Eicosene Copolymer. The formula with Dermacryl AQF polymer has excellent spray aesthetics and less particle drift resulting in more uniform coverage.

Example 4

Broad Spectrum Water Resistant Sunscreen Lotion

| Ingredient | INCI name | % w/w Formula 7 |
|---|---|---|
| Phase A | | |
| Deionized water | | 47.70 |
| Disodium EDTA | | 0.10 |
| Carbopol 940(2% solution) | Carbomer | 15.00 |
| Propylene glycol | | 2.00 |
| Dermacryl AQF (45% active) polymer | | 4.40 |
| Phase B | | |
| Corapan TQ | Diethylhexyl naphthalate | 5.00 |
| Parsol 1789 | Avobenzone | 3.00 |
| Neo Heliopan BB | Benzophenone-3 | 4.00 |
| Neo Heliopan OS | Octyl salicylate | 5.00 |
| Neo Heliopan HMS | Homosalate | 5.00 |
| Finsolv TN | C12-15 alkyl benzoate | 5.00 |
| Brij 721 | Steareth-21 | 1.00 |
| Brij 72 | Steareth-2 | 0.80 |
| Protachem GMS-450 | Glyceryl stearate | 1.00 |
| Phase C | | |
| Triethanolamine | | q.s. to pH 6.5 |
| Phase D | | |
| Phenonip | | 1.00 |

Mixing procedure: Phase A ingredients were combined at room temperature with moderate propeller mixing. Phase A was then heated to 75° C. Phase B ingredients were combined and heated 75° C. with propeller mixing. When both Phase A and B reached temperature, B was added to A with vigorous propeller mixing. The mixture was then cooled to below 40° C. with moderate propeller mixing, the pH was adjusted with TEA, and Phenonip was added and mixed until uniform.

Example 5

Water Resistant Sunscreen with ZnO

| Ingredient | INCI name | % w/w Formula 8 |
|---|---|---|
| Phase A | | |
| Arlacel 165 | Glyceryl stearate (and) PEG-100 stearate | 3.50 |
| Montanov S | Cocoglucoside (and) coconut alcohol | 1.30 |
| | Isodecyl neopentanoate | 8.00 |
| Neo Heliopan OS | Ethylhexyl salicylate | 5.00 |
| Escalol 567 | Benzophenone-3 | 3.00 |
| Neo Heliopan AV | Ethylhexyl methoxycinnamate | 7.50 |
| Zinc oxide neutral | Zinc oxide | 7.00 |
| Dow 345 | Cyclomethicone | 5.00 |
| Phase B | | |
| Keltrol CGT | Xanthan Gum | 0.25 |
| Veegum Ultra | Magnesium aluminum silicate | 1.50 |

-continued

| Ingredient | INCI name | % w/w Formula 8 |
|---|---|---|
| D.I. Water | Water | 52.35 |
| Tetrasodium EDTA | | 0.20 |
| Dermacryl AQF (45% active) polymer | | 4.40 |
| Phase C | | |
| Phenonip | | 1.00 |

Mixing Procedure: All ingredients in Phase A were combined, except Zinc oxide and Dow 345, and heated to 75-80° C. Zinc oxide was dispersed into the above portion of Phase A. Phase B was combined and all solid ingredients were dispersed in water completely. Phase B was heated to 75° C. When both Phase A and B reached temperature, A was added to B and homogenized for 5 minutes. Cooling was started with continuously mixing. Dow 345 was added at 65° C. and homogenized for 5 minutes more. The mixture was cooled with moderate stirring and Phase C was added when the temperature dropped below 40° C.

Example 6

Water Resistant Sunscreen with $TiO_2$

| Ingredient | INCI name | % w/w Formula 9 |
|---|---|---|
| Phase A | | |
| D.I. water | Water | 50.40 |
| Disodium EDTA | | 0.10 |
| Phenonip | | 1.00 |
| 1,2 Propanediol | Propylene glycol | 3.00 |
| Keltrol CG-RD | Xanthan gum | 0.35 |
| CMC 7LF | Cellulose Gum | 0.05 |
| Dermacryl AQF (45% active) polymer | | 4.40 |
| Phase B | | |
| Neo Heliopan AV | Ethylhexyl methoxycinnamate | 7.50 |
| Neo Heliopan BB | Benzophenone-3 | 2.00 |
| MT-500B-MS5 | TiO2 + methicone | 11.00 |
| Myritol 318 | Caprilic/capric triglyceride | 9.00 |
| DC 345 | Cyclomethicone | 3.50 |
| Finsolv TN | C12-15 alkyl benzoate | 1.50 |
| Vitamin E acetate | Tocopheryl acetate | 0.20 |
| Amphisol | DEA-cetyl phosphate | 2.50 |
| Brij 72 | Steareth-2 | 1.85 |
| Brij 721 | Steareth-21 | 0.65 |
| Protachem GMS-450 | Glyceryl stearate | 1.00 |

Mixing procedure: Phase A ingredients were combined at room temperature with moderate propeller mixing. After making sure that the gums were well dispersed, heating was started to 70-75° C. Phase B ingredients were combined and mixed vigorously for 20 minutes, allowing for a good dispersion of $TiO_2$. Phase B was heated to 75-80° C. with propeller mixing. When both Phase A and B reached temperature, B was added to A with vigorous propeller mixing. The temperature was kept at 75° C. for an additional 15-20 minutes while mixing thoroughly. Phase C was then added, mixed and cooled to ambient temperature.

Example 7

In-Vivo Very Water Resistant Sunscreen Test Results

A 5 subject panel was tested per the FDA final monograph ("Sunscreen Drug Products for Over-The-Counter Human Drugs," Rule, 21 CFR Part 352, Subpart D (Federal Register/ Vol. 64, No. 98/Friday May 21, 1999, Proposed Amendment; Docket number 78N-0038/CP12, Jun. 21, 1999) for very water resistant sunscreens. A formula containing DERMACRYL AQF film forming polymer was compared with the base formula containing no polymer (blank). The formulas were evaluated after an 80 minute immersion in water. The results are described below (Table 1).

TABLE 1

In-Vivo Test Results

| | Blank no polymer | Formula 1 DERMACRYL AQF |
|---|---|---|
| Static | 32 | 32 |
| Post Immersion | <21 | 31 |
| Standard Deviation | 0 | 1.15 |

Example 8

In-Vitro Very Water Resistant Sunscreen Test Results

The In-Vitro sunscreen waterproof/water resistance test method: Vitro-Skin N-19 (available from IMS Inc.) was used as the substrate for this test. Labsphere UV 1000S ultraviolet transmittance analyzer was use to measure the SPF values. Vitro-skin had been hydrated prior to use in a hydration chamber with humidity regulated by the solution of water/ glycerin at 23° C. for 16 hours. Sunscreen was then applied onto the hydrated vitro-skin (6.2 cm×9.0 cm each piece), with the product dose of 2 ul/cm$^2$. Initial SPF value was then measured, followed by immersing the samples in water bath, and setting the stirring motor to 300 rpm. For waterproof or very water resistance test, the samples were immersed in water for 80 minutes. The SPF after water immersion was then measured after excess water had been removed from the samples and after the samples were equilibrated in the chamber for 2 hours. Each test sample was run in triplicate, and each vitro-skin was scanned 10 times when SPF was measured.

| Formulation | SPF (after 80 min in H2O) | % SPF Retention after immersion* | SPF value enhancement over blank** (after 80 min in H2O) |
|---|---|---|---|
| Formula 2 | 30.2 (0.9)*** | 100% | 25.6 |
| Formula 3 | 33.5 (1.1) | 100% | 15.6 |
| Formula 7 | 37.3 (2.2) | 86% | 32.5 |
| Formula 8 | 51.9 (0.8) | 100% | 41.6 |

*% SPF Retention after immersion = SPF (after 80 minutes in water)/SPF (initial, before 80 minutes in water)
**SPF value enhancement over blank = SPF (formula with Dermacryl AQF polymer) − SPF (same formula without Dermacryl AQF polymer)
***Standard Deviation

Example 9

Sunscreen Aqueous Gel Containing Dermacryl AQF—Cold Process

| Ingredient | INCI name | % w/w Formula 10 |
|---|---|---|
| Phase A | | |
| Neo Heliopan Hydro | Phenylbenzimidazole Sulfonic Acid | 5.00 |
| Deionized water | | 10.0 |
| TEA 99% | Triethanolamine | 5.5 |
| Phase B | | |
| D.I. Water | Water | q.s. |
| Disodium EDTA | | 0.10 |
| Structure XL | Hydroxypropyl Starch Phosphate | 5.0 |
| Escalol 587 | Benzophenone-4 | 3.0 |
| Dermacryl AQF (45% active) polymer | Acrylates Copolymer | 4.40 |
| Phase C | | |
| Germaben II | | 1.00 |

Mixing Procedure: Neo Heliopan Hydro and the water were preheated. Triethanolamine was added and mixed well. The ingredients of phase B were then combined in order and mixed until homogeneous. Phase A was added to B and mixed until homogeneous. Phase C was added to the batch with mixing.

Example 10

Face Foundation

| Ingredient | INCI name | % w/w Formula 11 |
|---|---|---|
| Phase A | | |
| D.I. water | Water | q.s. |
| Polyglycol E-400 | PEG-8 | 5.0 |
| 1,2 Propanediol | Propylene glycol | 5.0 |
| Dermacryl AQF (45% active) polymer | Acrylates copolymer | 4.40 |
| Phase B | | |
| Ceraphyl 140A | Decyl oleate | 2.2 |
| Cerasynt Q | Glyceryl monostearate SE | 0.9 |
| Sorbitan stearate | Sorbitan stearate | 1.5 |
| Stearyl alcohol | Stearyl alcohol | 0.5 |
| Phase C | | |
| Iron oxide | | 2.0 |
| Titanium dioxide | | 6.0 |
| Kaolin | | 7.0 |
| Phase D | | |
| DC 345 | Cyclomethicone | 15.0 |
| Phase E | | |
| Preservative | | q.s. |

Mixing Procedure: Phase A and phase B were combined separately and heated to 75° C. Phase B was added to A with good mixing. The mixture was cooled with continued mixing to 60° C. and added phase C, then phase D was added. The mixture was mixed and cooled to less than 40° C. Phase E was added and then homogenized for 1-2 minutes.

In this face foundation, or any other color cosmetic products, Dermacryl AQF offers extended wear, crease resistance, and water resistance.

Example 11

Skin Moisturizer

| Ingredient | INCI name | % w/w Formula 12 |
|---|---|---|
| Phase A | | |
| Tegin M | Glycerin monostearate | 0.95 |
| Stearic acid | Stearic acid | 1.9 |
| Finsolv TN | C12-15 Alkyl Benzoate | 2.5 |
| Miglycol 812 | Caprilic/Capric Triglyceride | 3.0 |
| Isopropyl Myristate | Isopropyl Myristate | 2.5 |
| Jojoba oil | Jojoba oil | 2.0 |
| Phase B | | |
| Deionized water | | q.s. |
| TEA 99% | Triethanolamine | 0.35 |
| Glycerin | Glycerin | 3.0 |
| Xanthan gum | | 0.6 |
| Phase C | | |
| Dermacryl AQF (45% active) polymer | Acrylates copolymer | 4.40 |
| Phase D | | |
| Preservative | | q.s. | a) Mixing procedure: Phase A was combined and heated to 75° C. Phase B and Dermacryl AQF were mixed to ensure that the xanthan gum was fully dispersed, then heated to 75° C. Phase A was added to B with good mixing. The mixture was cooled with continued mixing to below 40° C., phases C and D were then added.

b) The mixing procedure of (a) was repeated except that Dermacryl AQF was added at 75° C. after combining phase A and B.

In this formula, Dermacryl AQF polymer acts as a film former to provide moisture protection or moisturization by maintaining occlusivity, in addition to extending the wear (including water resistance) of the product.

We claim:

1. A personal care composition comprising a water-proofing effective amount of a water dispersible acrylate copolymer emulsion having essentially no hydrophobic monomers having an alkyl group of greater than or equal to C8,
    wherein the copolymer is readily dispersible in the personal care composition at any point during processing without the need for additional processing,
    wherein the acrylate copolymer comprises from about 38% to about 48% butyl acrylate, from about 39% to about 49% methyl methacrylate, and from about 8% to about 18% methacrylic acid, by weight of the copolymer.

2. The composition of claim 1, wherein the acrylate copolymer is anionic at a pH above about 4.

3. The composition of claim 1 wherein the composition is a suncare composition.

4. The composition of claim 1 wherein the acrylate copolymer is not neutralized.

5. The composition of claim 1 wherein the composition is a skin care composition.

6. The composition of claim 1 wherein the composition is an emulsion.

7. The composition of claim 1 further comprising an anionic surfactant.

8. The composition of claim 1 wherein the acrylate copolymer is in the form of a 45% polymer-in-water emulsion.

* * * * *